(12) United States Patent
Potter

(10) Patent No.: US 10,478,597 B2
(45) Date of Patent: *Nov. 19, 2019

(54) MEDICAL CATHETER WITH DEFLECTION PULL RING AND DISTAL TIP ATTACHMENT APPARATUS

(71) Applicant: St. Jude Medical, Atrial Fibrillation Division, Inc., St. Paul, MN (US)

(72) Inventor: Daniel J. Potter, Stillwater, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 273 days.

This patent is subject to a terminal disclaimer.

(21) Appl. No.: 15/585,195

(22) Filed: May 3, 2017

(65) Prior Publication Data

US 2017/0296787 A1 Oct. 19, 2017

Related U.S. Application Data

(60) Continuation of application No. 13/555,918, filed on Jul. 23, 2012, now Pat. No. 9,642,985, which is a
(Continued)

(51) Int. Cl.
*A61B 18/14* (2006.01)
*A61M 25/01* (2006.01)
*A61B 17/00* (2006.01)

(52) U.S. Cl.
CPC ..... *A61M 25/0147* (2013.01); *A61B 18/1492* (2013.01); *A61B 2017/003* (2013.01);
(Continued)

(58) Field of Classification Search
CPC .......... A61B 18/1492; A61B 2017/003; A61B 2018/1472; A61M 2025/015; A61M 25/0147
See application file for complete search history.

(56) References Cited

U.S. PATENT DOCUMENTS 4,149,535 A * 4/1979 Volder ................ A61M 5/1582
604/164.01
4,471,779 A * 9/1984 Antoshkiw ...... A61B 17/12109
604/907

(Continued)

FOREIGN PATENT DOCUMENTS

WO WO 1996/039966 12/1996

*Primary Examiner* — Michael F Peffley
*Assistant Examiner* — Amanda L Zink
(74) *Attorney, Agent, or Firm* — Dykema Gossett PLLC

(57) ABSTRACT

A medical catheter includes a deflectable and compressible catheter shaft; a pull ring near a distal end of the catheter shaft; a distal tip that includes a tip element and a mounting shaft; and an attachment apparatus for securely attaching the distal tip to the catheter shaft, the attachment apparatus including a compression ring which compresses the catheter shaft and the mounting shaft together. The compression ring can be located around the catheter shaft to compress the catheter shaft against an outer surface of the mounting shaft, or within the catheter shaft to compress the catheter shaft outwardly against an inner surface of the mounting shaft. The catheter can be a non-irrigated ablation catheter, with the tip element being a tip electrode, and it can be an irrigated ablation catheter, with the distal tip including a fluid manifold.

21 Claims, 4 Drawing Sheets

Related U.S. Application Data division of application No. 11/963,393, filed on Dec. 21, 2007, now Pat. No. 8,226,641.

(52) U.S. Cl.
CPC ................ *A61B 2018/1472* (2013.01); *A61M 2025/015* (2013.01)

(56) References Cited

U.S. PATENT DOCUMENTS

| | | | |
|---|---|---|---|
| 4,778,447 A * | 10/1988 | Velde | A61M 39/10 604/29 |
| 5,114,403 A | 5/1992 | Clarke et al. | |
| 5,273,535 A | 12/1993 | Edwards et al. | |
| 5,389,073 A | 2/1995 | Imran | |
| 5,391,147 A | 2/1995 | Imran et al. | |
| 5,431,168 A | 7/1995 | Webster, Jr. | |
| 5,462,527 A | 10/1995 | Stevens-Wright et al. | |
| 5,478,330 A | 12/1995 | Imran et al. | |
| 5,533,967 A | 7/1996 | Imran | |
| 5,545,200 A | 8/1996 | West et al. | |
| 5,588,964 A | 12/1996 | Imran et al. | |
| 5,666,970 A | 9/1997 | Smith | |
| 5,715,817 A | 2/1998 | Stevens-Wright et al. | |
| 5,882,233 A | 3/1999 | Idehara | |
| 6,113,572 A | 9/2000 | Gailey et al. | |
| 6,508,810 B1 * | 1/2003 | Ouchi | A61B 1/00091 239/491 |
| 6,926,669 B1 | 8/2005 | Stewart et al. | |
| 7,229,437 B2 | 6/2007 | Johnson et al. | |
| 7,662,152 B2 | 2/2010 | Sharareh et al. | |
| 7,686,802 B2 | 3/2010 | Stevens-Wright | |
| 7,766,394 B2 * | 8/2010 | Sage | A61B 5/6864 285/276 |
| 7,815,635 B2 * | 10/2010 | Wittkampf | A61B 18/1492 606/41 |
| 8,515,521 B2 | 8/2013 | Erdman et al. | |
| 2003/0078571 A1 | 4/2003 | Sliwa et al. | |
| 2004/0193152 A1 * | 9/2004 | Sutton | A61B 18/1477 606/48 |
| 2006/0184165 A1 | 8/2006 | Webster, Jr. et al. | |
| 2007/0016167 A1 | 1/2007 | Smith et al. | |
| 2007/0250056 A1 | 10/2007 | Vanney | |
| 2007/0270679 A1 | 11/2007 | Nguyen | |
| 2008/0045943 A1 | 2/2008 | Wittkampf et al. | |
| 2011/0238040 A1 * | 9/2011 | Johnson | A61B 5/6864 604/524 |
| 2013/0046251 A1 * | 2/2013 | Jones | A61M 5/322 604/241 |

\* cited by examiner

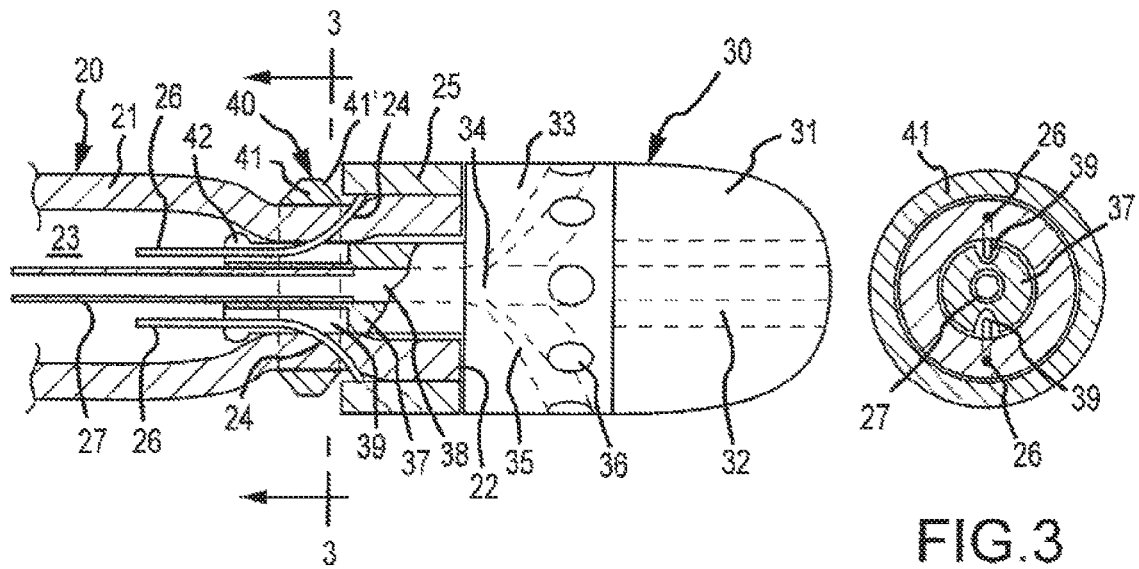
FIG.2
FIG.3
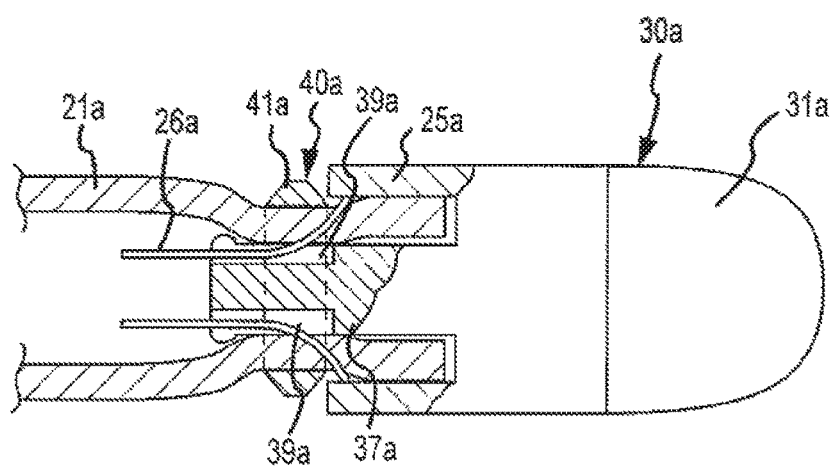
FIG.4

MEDICAL CATHETER WITH DEFLECTION PULL RING AND DISTAL TIP ATTACHMENT APPARATUS

CROSS-REFERENCE TO RELATED APPLICATIONS

This application is a continuation of U.S. application Ser. No. 13/555,918, filed on 23 Jul. 2012 (the '918 application), now U.S. Pat. No. 9,642,985, which is a division of U.S. application Ser. No. 11/963,393, filed on 21 Dec. 2007 (the '393 application), U.S. Pat. No. 8,226,641. The '918 application and the '393 application are both hereby incorporated by reference as though fully set forth herein.

BACKGROUND OF INVENTION

Field of Invention

The present invention relates to medical catheters, and in particular to ablation catheters which utilize a deflection pull ring near the distal end of a deflectable catheter shaft to bend the catheter shaft and the distal tip attached thereto in a desired direction.

The Prior Art

Medical catheters used in the diagnosis and treatment of various medical conditions are in common use throughout the world. They generally include a deflectable catheter shaft; a handle actuator which supports a proximal end of the catheter shaft; a pull ring assembly which includes a deflection pull ring positioned near the distal end of the catheter shaft and pull wires which extend from the pull ring to the handle actuator; and a distal tip with specialized tip element connected to the distal end of the catheter shaft. Pulling of the pull wires by operation of the handle actuator will tilt or rock the deflection pull ring and cause the catheter shaft to bend in a desired fashion.

Ablation catheters are a category of medical catheters used to ablate tissue, e.g., in the treatment of heart malfunctions. They can be irrigated (discharge ablation fluid in addition to ablation energy) or non-irrigated (no discharge of ablation fluid therefrom). Their distal tip will include a tip electrode and an energy source is connected to their handle actuator to supply energy to their tip electrode. In irrigated ablation catheters a fluid manifold is attached to, or is one-piece with, the tip electrode, and a fluid source is attached to their handle actuator to supply ablating fluid thereto. Their distal tip can include a mounting shaft which cooperates with the distal end of the adjacent deflectable catheter shaft for connection thereto.

However, in many medical catheters, including irrigated and non-irrigated ablation catheters, the distal tips are attached to the distal ends of the catheter shafts using adhesives. It has been found that over time these adhesives can lose their adhesion properties, and the distal tips can become loose. This is a dangerous situation that must be avoided.

Also, recurring tilting and rocking of the pull rings by operation of the handle actuators can cause the pull rings to creep along the catheter shafts towards the handle actuators and away from the distal ends, thus resulting in decreased effectiveness in deflecting the catheter shaft in the desired manner.

It is an object of the present invention to provide an attachment apparatus for attaching a distal tip to a catheter shaft of a medical catheter which will reliably connect the distal tip to the catheter shaft.

It is another object of the present invention to provide an attachment apparatus for attaching a distal tip to a catheter shaft of a medical catheter which will prevent creeping of the pull ring along the catheter shaft.

It is a still further object of the present invention to provide an attachment apparatus that will achieve the foregoing results in either an irrigated or non-irrigated ablation catheter.

SUMMARY OF INVENTION

The foregoing objects are achieved with attachment apparatus which includes a compression ring that compresses the catheter shaft against a mounting shaft of the distal tip to reliably connect the catheter shaft and the distal tip together. In one embodiment, the compression ring compresses the catheter shaft inwardly against an outer surface of the mounting shaft. In another embodiment, the compression ring compresses the catheter shaft outwardly against an inner surface of the mounting shaft. When positioned outside of the catheter shaft and between the pull ring and the handle actuator, the compression ring can provide an abutment that prevents creeping of the pull ring towards the handle actuator during use.

The attachment apparatus can include an outwardly-extending feature, such as an annular lip, on the mounting shaft to prevent slippage of the mounting shaft past the compression ring. The attachment apparatus can also include features such a surface irregularities (e.g., barbs) on the outer surface of the mounting shaft to grip an interior surface of the catheter shaft, or features such as surface irregularities (e.g., barbs) on an interior surface of the mounting shaft to grip the outer surface of the mounting shaft extending therein. In still another embodiment, the compression ring can be an insert within the catheter shaft which is otherwise gripped on its outer surface by a mounting shaft of the distal tip.

Further aspects and advantages of this invention will be better understood by reference to the attachment drawings, taken in conjunction with the following discussion.

BRIEF DESCRIPTION OF THE DRAWINGS

FIG. 2 is an enlarged side view, partially in section, of the distal end portion of the deflectable catheter shaft, the distal tip and the attachment apparatus of the irrigated ablation catheter assembly of FIG. 1;

FIG. 3 is a sectional view of FIG. 2 as seen along line 3-3 therein;

FIG. 4 is a side view, partially in section, of a distal end portion of a deflectable catheter shaft, a distal tip and an attachment apparatus of a non-irrigated ablation catheter assembly according to a second embodiment of the present invention;

DETAILED DESCRIPTION OF THE PREFERRED EMBODIMENTS

Figure 1:
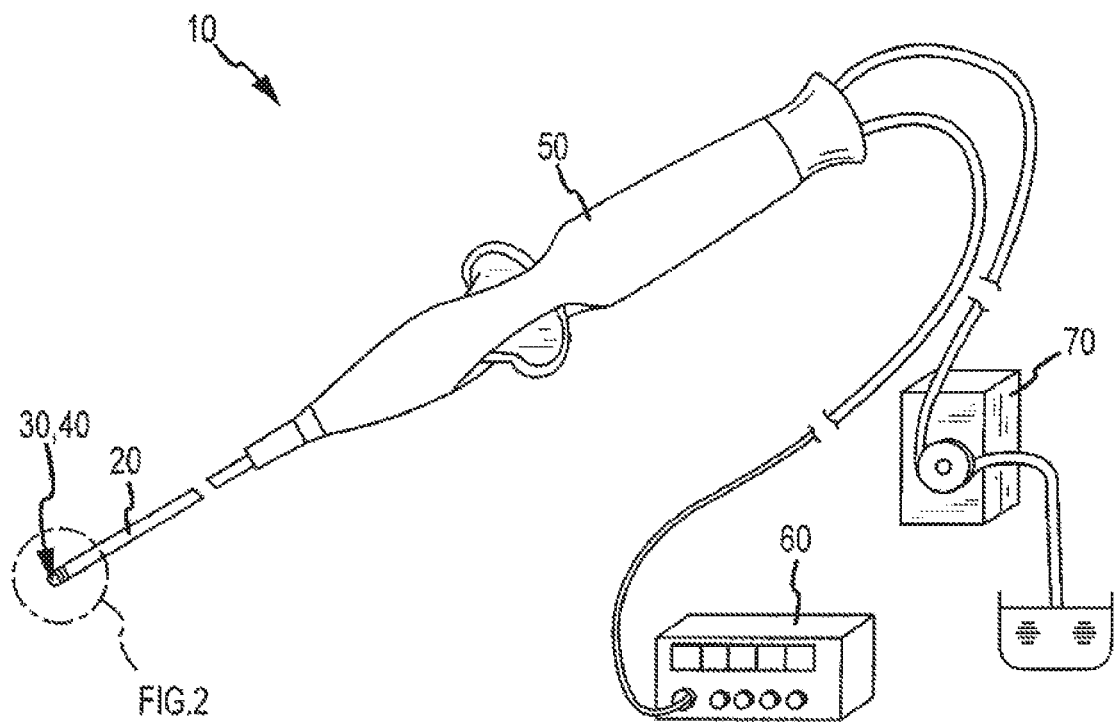
FIG. 1 is an isometric view of an irrigated ablation catheter system which includes an irrigated ablation catheter assembly according to a first embodiment of the present invention.

FIG. 1 shows an irrigated ablation catheter system 10 according to an embodiment of the present invention. It includes an ablation catheter assembly comprised of an ablation catheter 20, a distal tip 30 attached to the distal end portion of the ablation catheter by attachment apparatus 40, and a handle actuator 50 which supports the proximal end of the ablation catheter 20. As part of the irrigated ablation catheter system 10, an energy source 60 and a fluid source 70 are connected to the handle actuator 50 to supply energy and fluid to the distal tip 30 via the catheter 20.

FIGS. 2 and 3 show a distal end portion of the catheter 20, the distal tip 30 and the attachment apparatus 40. The catheter 20 includes a bendable and compressible catheter shaft 21 that defines a distal end 22 and a hollow interior 23. Guide channels 24 extend through the wall of the catheter shaft at diametrically opposed locations near the distal end 22. A pull ring assembly includes a deflection pull ring 25 positioned around the shaft 21 near its distal end 22, and pull wires 26 attached to diametrically opposed locations on the pull ring which extend through the guide channels 24 into the hollow interior 23 and back to the handle actuator 50. The pull wires 26 are respectively pulled by manual operation of triggers of the handle actuator 50 to cause the pull ring 25 to tilt or rock relative to the catheter shaft and thereby bend the distal end portion of the catheter shaft in a first direction or in a second, opposite direction in a known manner. A fluid delivery tube 27 extends from the handle actuator 50 through the hollow interior 23 towards the distal end 22 and is supplied with fluid by the fluid source 70.

The distal tip 30 includes a tip electrode 31, a fluid manifold 33 and a mounting shaft 37. The mounting shaft 37 is one piece with the fluid manifold 33 and it extends into the hollow interior 23 of the catheter shaft. It includes a central axial passageway 38 into which the fluid delivery tube 27 sealingly extends, as well as axial channels 39 in its outer surface at diametrically opposed locations and in which the pull wires 26 can extend.

The fluid manifold 33, which is cylindrical in shape, defines a central axial passageway 34 which is an extension of the axial passageway 38, and channels 35 that extend from the axial passageway 34 to orifices 36 spaced around its periphery. Fluid supplied to the axial passageway 38 from the fluid delivery tube 27 will flow to the axial passageway 34, then through channels 35 to orifices 36 to be discharged therefrom. In an alternate embodiment the fluid manifold will include only one channel 35 leading to one orifice 36.

The tip electrode 31 can include channels 32 (indicated in FIG. 2 with dashed lines) to deliver fluid from the axial passageway 34 to the distal end thereof (in an alternate embodiment only one channel is provided). The tip electrode 31 is connected to the fluid manifold in known ways, such as with adhesive, and can be made of well-known materials, such as platinum.

The attachment apparatus 40 includes a compression ring 41 which is positioned around the catheter shaft 21 adjacent the pull ring 25 between the pull ring and the handle actuator 50. The compression ring 41 is sized to compress the catheter shaft 21 against the mounting shaft 37 to secure the fluid manifold 33 and the tip electrode 31 to the distal end portion of the catheter shaft. It also provides an abutment against movement of the pull ring 25 towards the handle actuator 50 which can occur due to repeated tilting of the pull ring by pull wires 26. The compression ring 41 defines an inclined surface 41' facing the pull ring 25 so that movement of the pull ring against the surface 41' will cause the pull ring to further compress the catheter shaft 21 against the mounting shaft 37.

The attachment apparatus also includes an outwardly-projecting surface feature in the form of an annular lip 42 on a free end of the mounting shaft 37 in the hollow interior 23. The outwardly-projecting annular lip 42 is positioned closer to the handle actuator 50 than the compression ring 41 so as to help prevent release of the mounting shaft 37 (and thus the distal tip as a whole) away from the catheter shaft. Indeed, the outwardly-projecting annular lip 42 will cause the mounting shaft 37 (and thus the distal tip as a whole) to snap fit past the compression ring 41 during mounting of the distal tip to the catheter 20.

Turning now to the embodiment of ablation catheter of FIG. 4, wherein like elements to the embodiment of FIGS. 1-3 have like reference numbers, it can be seen that the tip electrode 31a includes a pull ring 25a in the form of a cylindrical skirt that is one-piece with the tip electrode (no fluid manifold is present). Pulling of the pull wires 26a by the handle actuator (not shown) will cause the distal tip 30a to be directly moved in a first or opposite second direction. Compression ring 41a of attachment apparatus 40a compresses deflectable and compressible catheter shaft 21a against the mounting shaft 37a to secure them together.

Figures 5, 6:
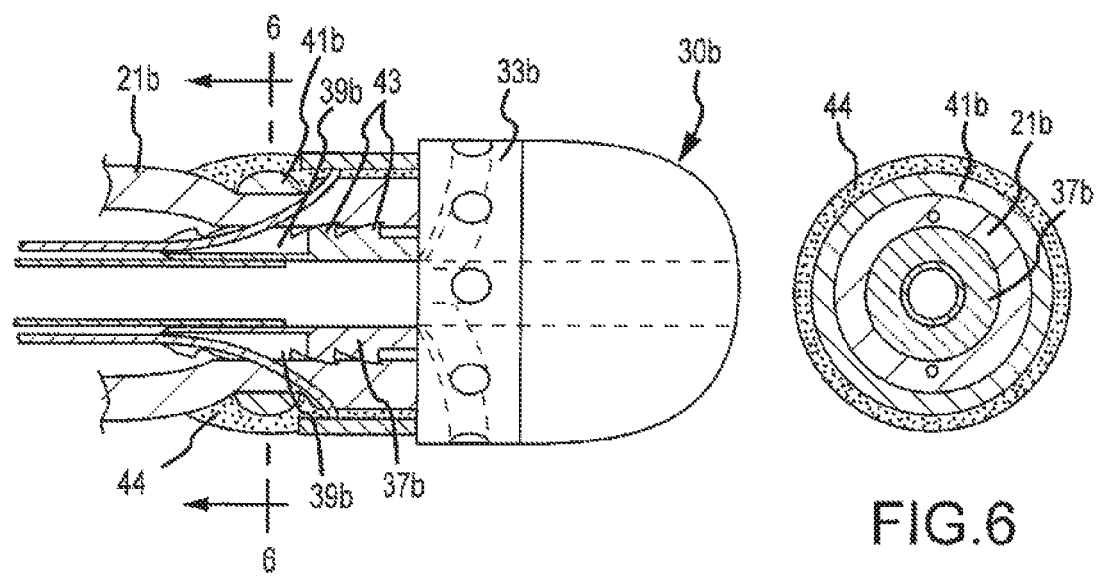
FIG. 5 is a side view, partially in section, of a distal end portion of a deflectable catheter shaft, a distal tip and an attachment apparatus of an irrigated ablation catheter assembly according to a third embodiment of the present invention.
FIG. 6 is a sectional view of FIG. 5 as seen along line 6-6 therein.

In the embodiment of ablation catheter shown in FIGS. 5 and 6, wherein like elements to the embodiment of FIGS. 1-3 have like reference numbers, the mounting shaft 37b does not include a projecting annular lip but instead includes barbs 43 on its outer surface which grip the deflectable and compressible catheter shaft 21b compressed thereagainst by the compression ring 41b. Trim adhesive 44 covers the compression ring 41b and extends between the electrode pull ring 25b and both the catheter shaft 21b and the fluid manifold 33b. The trim adhesive provides a smooth outer surface to the catheter 20. The barbs 43 could be replaced by other features or surface irregularities for gripping the catheter shaft.

Figure 7:
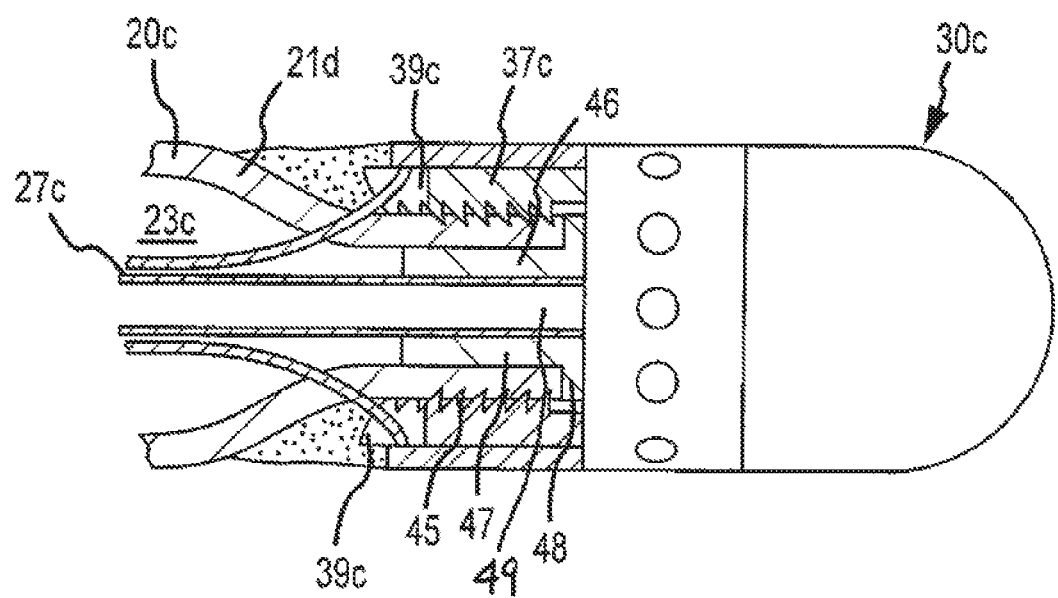
FIG. 7 is a side view, partially in section, of the distal end portion of a deflectable catheter shaft, a distal tip and an attachment apparatus of an irrigated ablation catheter assembly according to a fourth embodiment of the present invention.

In the FIG. 7 embodiment of deflectable ablation catheter, wherein like elements to the embodiment of FIGS. 1-3 have like reference numbers, the mounting shaft 37c includes barbs 45 on its inner surface which grip the distal end portion of the catheter shaft 21c that extends therein, and a T-shaped reinforcement element 46 having a cylindrical body 47, a rim 48 and an axial passageway 49 therethrough is positioned in the hollow interior 23c of the catheter shaft. The cylindrical body 47 functions as a compression ring to compress the catheter shaft 21c against the barbs 45 and provide a secure attachment of the distal tip 30d to the catheter 20c. The barbs 45 could be replaced by other features or surface irregularities that grip the catheter shaft.

While a number of embodiments of the invention have been shown and described, modifications therein can be made and still fall within the scope of the appended claims. For example, instead of the pull rings having two pull wires connected thereto, three, four or more wires could be connected thereto around its circumference, with corresponding guide channels being provided in the catheter shaft and corresponding axial grooves provided in the mounting shaft. Also, the pull ring could function as an electrode and the pull wires could be energy conducting so as to deliver energy to the pull ring from energy source 60. The attachment apparatus could include multiple compression ring systems positioned adjacent one another. And trim adhesive could be utilized in the FIG. 2-3 embodiment to provide a smooth outer surface to the catheter shaft.

What is claimed is:

1. A catheter assembly, comprising:
   a distal tip having an axis and including a tip element and a mounting shaft wherein said mounting shaft has an axial passageway extending therethrough and an inner surface that includes a protrusion;
   an elongate member having a distal end thereof extending into said axial passageway of said mounting shaft wherein said elongate member bears against said protrusion of said mounting shaft; and
   a reinforcement element positioned within a hollow interior of said elongate member that compresses said elongate member against said inner surface of said mounting shaft.

2. The catheter assembly of claim 1 wherein said elongate member is coupled to said mounting shaft by said protrusion.

3. The catheter assembly of claim 1 wherein said protrusion comprises a plurality of barbs on said inner surface of said mounting shaft that grip said distal end of said elongate member extending into said axial passageway.

4. The catheter assembly of claim 1 wherein said tip element includes a discharge orifice on an external surface thereof and wherein said elongate member comprises a fluid lumen, said tip element being configured to deliver a fluid from said fluid lumen to said discharge orifice.

5. The catheter assembly of claim 4 wherein said tip element comprises a plurality of discharge orifices on said external surface wherein said tip element is configured to deliver said fluid from said fluid lumen to said plurality of discharge orifices.

6. The catheter assembly of claim 5 wherein said discharge orifices are distributed around a circumference of said external surface.

7. The catheter assembly of claim 5 wherein said tip element comprises a manifold in fluid communication with said fluid lumen.

8. The catheter assembly of claim 7 wherein said plurality of discharge orifices are in fluid communication with said manifold through a respective plurality of fluid delivery channels.

9. The catheter assembly of claim 1 wherein said mounting shaft is integral with said tip element.

10. The catheter assembly of claim 1 wherein said protrusion is integral with said mounting shaft.

11. The catheter assembly of claim 1 wherein said reinforcement element comprises a cylindrical body positioned in said hollow interior of said elongate member.

12. The catheter assembly of claim 11 wherein said reinforcement element further comprises a rim extending from said cylindrical body to form a T-shaped reinforcement element.

13. The catheter assembly of claim 1 wherein said tip element comprises a tip electrode.

14. A medical device comprising:
    a handle;
    an elongate member having a proximal end and a distal end wherein said proximal end is coupled to said handle, said elongate member comprising a fluid lumen;
    a distal tip including a tip element and a mounting shaft, said mounting shaft having a passageway extending therethrough and an outer surface that includes a protrusion, said mounting shaft extending into a hollow interior of said distal end of said elongate member such that said protrusion bears against said elongate member,
    said tip element having at least one discharge orifice on an outer surface thereof that is in fluid communication with said fluid lumen.

15. The medical device of claim 14 including a fluid delivery tube having said fluid lumen that is sealingly connected to said mounting shaft to deliver fluid to said passageway of said mounting shaft.

16. The medical device of claim 14 wherein said distal tip further includes a manifold, said manifold being in fluid communication with said fluid lumen through said passageway of said mounting shaft.

17. The medical device of claim 16 wherein said manifold is cylindrical in shape and wherein a fluid channel extends from said manifold to said at least one discharge orifice.

18. The medical device of claim 16 wherein said tip element comprises a plurality of fluid channels extending from said manifold to a respective one of a plurality of discharge orifices positioned around a circumference of said tip element.

19. The medical device of claim 14 wherein said protrusion comprises a barb on said outer surface of said mounting shaft which grips said distal end of said elongate member.

20. The medical device of claim 19 wherein said protrusion comprises a plurality of barbs.

21. The medical device of claim 14 wherein said protrusion comprises an outwardly-projecting annular lip on said mounting shaft.

* * * * *